(12) United States Patent
Golden, Jr.

(10) Patent No.: US 9,498,395 B2
(45) Date of Patent: Nov. 22, 2016

(54) JOINT MOVEMENT DETECTION DEVICE AND SYSTEM FOR COORDINATING MOTOR OUTPUT WITH MANUAL WHEELCHAIR PROPULSION

(71) Applicant: Stephen C. Golden, Jr., Menasha, WI (US)

(72) Inventor: Stephen C. Golden, Jr., Menasha, WI (US)

(*) Notice: Subject to any disclaimer, the term of this patent is extended or adjusted under 35 U.S.C. 154(b) by 0 days.

(21) Appl. No.: 14/681,080

(22) Filed: Apr. 7, 2015

(65) Prior Publication Data

US 2015/0298765 A1     Oct. 22, 2015

Related U.S. Application Data

(60) Provisional application No. 61/980,552, filed on Apr. 16, 2014.

(51) Int. Cl.
  *A61G 5/10*   (2006.01)
  *A61G 5/04*   (2013.01)
  *A61B 5/00*   (2006.01)

(52) U.S. Cl.
  CPC ............ *A61G 5/10* (2013.01); *A61B 5/4528* (2013.01); *A61B 5/6824* (2013.01); *A61G 2005/048* (2013.01); *A61G 2203/30* (2013.01)

(58) Field of Classification Search
  CPC ............ A61G 5/10; A61G 2005/048; A61G 2203/30; A61B 5/4528; A61B 5/6824
  USPC ......................................................... 701/22
  See application file for complete search history.

(56) References Cited

U.S. PATENT DOCUMENTS

| | | |
|---|---|---|
| 4,050,533 A | 9/1977 | Seamone |
| 4,410,060 A | 10/1983 | Cunard |
| 4,422,515 A | 12/1983 | Loveless |
| 5,656,001 A | 8/1997 | Baatz |
| 5,910,714 A | 6/1999 | Buchanan |
| 6,050,357 A | 4/2000 | Lang |
| 6,059,062 A | 5/2000 | Lang |
| 6,112,837 A | 9/2000 | Kanno |
| 6,217,398 B1 | 4/2001 | Davis |
| 6,724,165 B2 | 4/2004 | Hughes |
| 6,731,086 B2 | 5/2004 | Nonaka |
| 6,946,650 B2 | 9/2005 | Yoerger |
| 7,261,309 B2 | 8/2007 | Watwood |
| D583,104 S | 12/2008 | Stewart |
| 7,791,309 B2 | 9/2010 | Hwang |
| 7,832,515 B2 | 11/2010 | Barthelt |
| 7,837,210 B2 | 11/2010 | Kylstra |
| 7,840,327 B2 | 11/2010 | Bitzer |
| 7,918,697 B2 | 4/2011 | Gulas |

(Continued)

FOREIGN PATENT DOCUMENTS

| | | |
|---|---|---|
| DE | 19848530 C1 | 2/2000 |
| WO | WO2005058685 A1 | 6/2005 |

(Continued)

*Primary Examiner* — Marc McDieunel
*Assistant Examiner* — James E Stroud

(57) ABSTRACT

A joint movement detection device and system is presented which is responsive to elbow or wrist movements during use of a manually-propelled wheelchair to enable coordination of assistive motor energization with a user's efforts at self-motivating the manually-propelled wheelchair during driving, steering, and braking of the wheelchair. Several embodiments are provided which help to ensure user-intended assistive motor output that is responsive to movement of the joint over which the device is worn.

20 Claims, 9 Drawing Sheets

(56) References Cited

U.S. PATENT DOCUMENTS

| | | | |
|---|---|---|---|
| 8,109,529 B2* | 2/2012 | Rand | A61G 5/022 280/244 |
| 8,244,655 B2 | 8/2012 | Hubbard | |
| 8,280,561 B2* | 10/2012 | Griggs | G05G 9/047 180/19.3 |
| 8,292,678 B2 | 10/2012 | Burgess, Jr. | |
| 8,306,673 B1 | 11/2012 | Manning | |
| 8,337,266 B2 | 12/2012 | Ellis | |
| 8,482,412 B2 | 7/2013 | Majoros | |
| 8,500,143 B2 | 8/2013 | Yu | |
| 8,567,547 B2 | 10/2013 | Kulatunga | |
| 8,572,764 B2 | 11/2013 | Thellmann | |
| 2002/0036105 A1 | 3/2002 | Birmanns | |
| 2003/0163287 A1 | 8/2003 | Amsbury | |
| 2004/0243025 A1* | 12/2004 | Peles | A61H 1/0277 601/5 |
| 2005/0006158 A1 | 1/2005 | Tsai | |
| 2005/0195166 A1* | 9/2005 | Cooper | G05G 9/047 345/161 |
| 2005/0271279 A1 | 12/2005 | Fujimura | |
| 2006/0079817 A1* | 4/2006 | Dewald | A61H 1/02 601/5 |
| 2006/0167564 A1* | 7/2006 | Flaherty | A61B 5/0476 623/57 |
| 2006/0187196 A1 | 8/2006 | Underkoffler | |
| 2008/0009771 A1* | 1/2008 | Perry | B25J 9/0006 600/587 |
| 2008/0065291 A1 | 3/2008 | Breed | |
| 2008/0129099 A1* | 6/2008 | Huang | A61G 5/006 297/362.12 |
| 2009/0095552 A1 | 4/2009 | Gulas | |
| 2010/0026484 A1 | 2/2010 | King | |
| 2010/0280629 A1* | 11/2010 | Jung | A61H 3/00 623/53 |
| 2011/0023920 A1 | 2/2011 | Bolton | |
| 2011/0061697 A1 | 3/2011 | Behrenbruch | |
| 2011/0201238 A1 | 8/2011 | Rott | |
| 2011/0266082 A1 | 11/2011 | Yang | |
| 2012/0279789 A1* | 11/2012 | Brill | A61G 5/047 180/6.5 |
| 2013/0008732 A1 | 1/2013 | Richter | |
| 2013/0019700 A1 | 1/2013 | Matsumoto | |
| 2013/0035010 A1 | 2/2013 | Boukas | |
| 2013/0197408 A1 | 8/2013 | Goldfarb | |
| 2013/0261871 A1 | 10/2013 | Hobbs | |
| 2013/0274635 A1 | 10/2013 | Coza | |
| 2013/0300662 A1 | 11/2013 | Liu | |
| 2014/0262575 A1 | 9/2014 | Richter | |
| 2014/0336781 A1* | 11/2014 | Katyal | A61F 2/72 623/25 |
| 2015/0025423 A1* | 1/2015 | Caires | A61H 1/024 601/35 |
| 2015/0142130 A1* | 5/2015 | Goldfarb | A61H 1/024 623/25 |
| 2015/0173993 A1* | 6/2015 | Walsh | A61H 3/00 414/4 |
| 2015/0265490 A1* | 9/2015 | Cestari Soto | A61H 3/04 297/5 |

FOREIGN PATENT DOCUMENTS

| | | |
|---|---|---|
| WO | WO2008036087 A1 | 3/2008 |
| WO | WO2010030822 A1 | 3/2010 |
| WO | WO2012118263 A1 | 9/2012 |
| WO | WO2013155112 A1 | 10/2013 |

* cited by examiner

JOINT MOVEMENT DETECTION DEVICE AND SYSTEM FOR COORDINATING MOTOR OUTPUT WITH MANUAL WHEELCHAIR PROPULSION

CROSS-REFERENCE TO RELATED APPLICATION

This application claims priority to U.S. Provisional Patent Appl. Ser. No. 61/980,552 filed Apr. 16, 2014, which is hereby incorporated by reference in its entirety for all purposes.

BACKGROUND OF THE INVENTION

1. Field of the Invention

The present invention concerns wheelchairs, related devices, and methods of use, particularly for personal mobility.

2. Description of Related Art

As an alternative to walking, jogging, or running to move about in the physical environment, the wheelchair serves as a suitable although limited transportation means and is a requirement of daily mobility for individuals with partial or complete impairment of sensory or motor function in the legs, hips, and lower torso.

During wheelchair propulsion, a user occupying a wheelchair engages in intermittent exertion of muscle-generated force at a lateral location relative to a longitudinal vertical plane passing through the center of the vehicle to direct the vehicle along a desired course. The user controls the speed and orientation of the wheelchair by gripping a pair of opposing pushrims, attached laterally to the drive wheels, with the hands and uses the arms to apply force against the opposing pushrims. During this process, contraction and relaxation of muscles in the user's arms and hands causes the elbow and wrist joints to undergo repeated and readily observable angular changes.

Propulsion of wheelchairs further involves the act of coasting, wherein the user occupying the wheelchair momentarily exerts muscle-generated force to propel the wheelchair and, following said exertion, the user assumes a relaxed, non-exerting disposition while the wheelchair continues moving along the desired course with the wheelchair bearing the full weight of the user.

Some wheelchairs alternatively employ levers, either attached to the wheel hubs or to the wheelchair frame, wherein the levers enable the transfer of muscle-generated forces to the wheels while also affording the user a propulsion and control means that does not require manual contact with the wheels, tires or pushrims. Such "lever-drive" systems may also serve to amplify human force via a drive train, such as with gears or sprockets, or simply by virtue of the mechanical advantage conferred by the length of the levers. Similar to the experience of using a pushrim-driven configuration, in the case of a lever-driven wheelchair the elbow and wrist joints likewise undergo repeated and readily observable angular changes.

The left and right sides of the wheelchair are driven in a substantially independent fashion so that forward bodily force exerted by the occupant, using a first arm, through a first drive wheel of the wheelchair produces forward movement of a first side of the wheelchair and little to no forward movement of a second side of the wheelchair. Likewise, forward bodily force exerted by the occupant, using a second arm, through a second, opposing drive wheel produces forward movement of the second side of the wheelchair and little to no forward movement of the first side of the wheelchair. Forces independently imparted to the opposing drive wheels thus enable the occupant to steer the wheelchair while also enabling braking and propulsion of the wheelchair along the desired course. In an alternative characterization thereof, motive forces are exerted by the user and imparted through rotation of each drive wheel, to the ground surface upon which the wheelchair rests, at substantially lateral locations relative to a longitudinal vertical plane passing through the center of the wheelchair.

Regardless of the manual propulsion means, a forwardly-directed force transmitted through rotation of each drive wheel to the ground surface is accompanied by rearward movement of the ground-contacting region of the drive wheel, resulting in forward movement of the respective side of the wheelchair. Through this method of operation, the wheelchair user is also afforded the ability to slow down, stop, turn, and reverse the wheelchair along its course, depending on the user's skill level, grip strength, overall limb and torso strength, coordination and balance. Forward propulsion over longer distances, navigating over obstacles in the outdoors, negotiating tight turns in confined spaces indoors, and an overall sense of awareness upon encountering surfaces both familiar and unfamiliar are all reflections of an intuitive process by which the concerted efforts of the left and right sides of the occupant's upper body regulate the speed and direction of travel of the wheelchair in a carefully controlled manner.

Active manual wheelchair users, upon encountering a variety of physical environments requiring different levels of physical exertion as well as varying degrees of maneuverability, experience a profound need for sufficient upper body strength, range of motion, and manual dexterity, as well as the ability to execute gross and fine motor movements simultaneously. Also inherent to wheelchair propulsion is the patterned repetition of movements required to attain and maintain a desired speed of travel: a practiced user instinctively applies the correct amount of forward push and at a pace that is appropriately measured to achieve and maintain the desired speed of travel, in response to an acquired sense of speed, acceleration, resistance due to friction of the tires contacting the ground, and the force of gravity acting against or in the direction of travel. The dynamic, kinematic and rhythmic components are, therefore, significant and interlaced aspects of wheelchair mobility.

SUMMARY OF THE INVENTION

A variety of useful and innovative assistive propulsion technologies available in the manual wheelchair marketplace rely on a user's exertion of force against the driving wheels, or pushrims attached thereto, to trigger energization and de-energization of at least one motorized wheel assembly. The rhythmic and kinematic aspects of wheelchair mobility, however, have been left unappreciated by such devices; there has existed an unanswered need to effectuate assistive motor control functions in coordination with hand and arm movements, during the driving, steering and braking of manually-propelled wheelchairs. Accordingly, a primary objective of the present invention is to attend to and detect angular joint movements for the purpose of harmonizing user-enacted muscle exertion with motorized propulsion.

Furthermore, there is a need for an assistive motor control system which encourages a user to self-motivate his or her wheelchair—that is, to actively contribute muscle-generated exertion towards achieving a desired speed and orientation of the wheelchair. Prior technologies have enabled users to travel faster and for greater distances, yet these devices have also permitted users to discontinue self-motivating their wheelchairs and to thus become de-conditioned away from engaging in the vigorous and beneficial exercises that are necessary for maintaining optimum physical strength and endurance for everyday wheelchair mobility and general well-being. The present disclosure advocates for reversing this trend through implementations wherein joint movement, during user-motivated manual wheelchair propulsion, is associated with energization of a motorized wheel for assisting the user in directing the wheelchair along the desired course.

With the aim of encouraging the user to self-motivate the wheelchair, wherein the user vigorously engages in propelling, steering and slowing the wheelchair, the present invention serves to exploit measured, rhythmic patterns or sequences involved in the process of momentary, stroke-based propulsion. A second aim herein is to preserve the rhythmic and kinematic aspects of wheelchair use—that is, to encourage user exertion without restricting, distracting from, or otherwise interfering with the user's ability to engage in the natural, patterned movements normally associated with using the wheelchair. Last, the present invention serves to optimize the allocation of human-generated and electromotive energy in a way that enhances the user's experience of motivating the wheelchair so that it is perceived as being smooth in operation and comfortable for the user.

Specifically, the present invention exploits the detectability of angular changes, occurring in the elbow or the wrist of an exertive-arm—an arm involved in the user's efforts at directing the wheelchair along a path, through propulsion in a forward or reverse direction, or through steering or slowing down—to regulate electro-motive output and to coordinate assistive motor energization with the user's efforts at self-motivating the wheelchair. Embodiments of the present invention may further exploit the repetition or rhythmic patterning of said angular changes occurring in the elbow or wrist of an exertive-arm to effectuate assistive motor control functions in coordination with hand and arm movements, during the driving, steering and braking of manually-propelled wheelchairs. The amplitude of power output provided by an assistive motor unit may, furthermore, be a function of a joint movement repetition, enacted by the user, such that the amplitude of power output is enabled, increased or stepped up towards a maximum allowed output amplitude following a series of joint movements.

For the purpose of appropriately and accurately energizing the assistive motor, detection of angular changes in the joint—or repetition thereof—may be interpreted or processed in conjunction with measurement of the amount of time which has elapsed between joint movement events and with measurement of vehicle dynamics such as speed, acceleration, or inclination. In addition, detection of a substantial increase in resistivity of the resistive sensor above a predetermined maximum resistivity value may prevent or halt motor energization and, similarly, detection of a substantial decrease in resistivity of the resistive sensor below a predetermined minimum resistivity value may prevent or halt motor energization, thereby helping to ensure a correct and user-intended assistive motor output that is reliably responsive to movement of the joint.

In addition to its involvement in propelling, steering, and slowing down, the exertive-arm may also be involved in effectuating other electro-motive control functions, including asymmetric application of assistive motorized propulsion, regenerative braking, and non-regenerative braking. It may be preferred, for example, to utilize the aforementioned control functions for the purpose of compensating for a lateral strength imbalance between the user's exertive-arm and an opposite arm, said opposite arm not having a joint-movement detection device attached thereto; this would be accomplished by associating exertive-arm joint movements with assistive motor propulsion that is biased more strongly towards either the left side or the right side of the wheelchair.

Arm and hand movements, enacted by a user to transfer muscle-generated drive force through each rear drive wheel, define a series of distinct elbow and wrist angular positions. Changes in angle position are detected with a deformable sensor incorporated into a joint-worn device, and these changes are interpreted by associated circuitry so as to efficiently and comfortably associate muscle-generated effort of the occupant with assistive motor output to achieve a desirable and beneficial output of hybrid human-electromotive power. The analog values received from the sensor are processed in order to accurately and appropriately generate an output signal for the purpose of motor energization.

Preferred embodiments include an intermediary digital logic gate or microcontroller configured for filtering out "noise" inherent to deformable resistive sensors, while also enabling more complex translation between sensor input and electro-motive output. Muscle-generated events and motor output events are correlated, that is—coordinated, synchronized, sequenced or otherwise intentionally timed or measured by way of automatic control logic in order to blend or harmonize electro-motive output with muscle-generated output in a manner which imparts continuity to the experience of propelling the wheelchair. Such an intermediary function is implemented using a generic integrated circuit or a programmable logic microcontroller, such as those manufactured by Atmel Corporation and Infineon Technologies, wherein generation of a rhythmic pattern by the user's muscles is coupled with motor energization and de-energization events. This enhanced integration or fusion of human movement patterning with electronic motor power control serves not to undermine the importance of the dynamic components of muscle-generated propulsion, such as strength and endurance, but rather to encourage such aspects of self-motivated power output, especially as a user becomes accustomed to the behavior and "feel" of the system in action.

A central objective of the inventive concept is, therefore, to enhance the relationship between a user-generated rhythmic propulsion pattern and a user-effectuated assistive control function to enable at least a loose association between the cyclical pattern of movements normally carried out by the user during manual wheelchair propulsion and assistive motor output. In some embodiments, for example, the system enables on-demand control over motor energization according to the arbitrary "whim" or desire of the user while also remaining responsive to joint movements during muscle-generated propulsion. In such a configuration, the system energizes and de-energizes the assistive motor in synchrony with repeated movements of the exertive-arm, but the user may willfully interrupt the pattern by extending and holding the wrist joint beyond an activating angle for a period of time necessary to rest before re-engaging in self-motivated propulsion. Other implementations enable a tighter association between motorized power output and the cyclical pattern of movements normally carried out by the user such as, for example, in a system which requires a series of consecutive movements, indicative of the user engaging in vigorous muscle-generated propulsion, before enabling assistive motor output.

Whether loosely or tightly associated, implementations enable complementary assistive propulsion in a way that preserves the function of the user's joints and muscles as well as the user's dexterity. Ideally, wearable structures are small and lightweight and are adapted for attachment to the user's arm or hand in a manner which conforms to the mechanics of the user's body in the context of normal wheelchair use, yet also optimizes the transduction of joint movement, via the resistive sensor, into an analog signal which may be filtered and interpreted by the processor. The sensor, for example is permanently or removably incorporated into the joint-worn garment, in a manner which optimally enables and is isolated towards detection of joint movement for the purpose of indicating user-intended effectuation of a control function. The confluence of the mechanical structures attached over the joint and the electronics contained within is thus crucial to the utility of the device or system.

Useful implementations are presented herein as sole assistive propulsion means for a wheelchair and as a novel joint kinematics-based control means for the purpose of enhancing and diversifying the user's experience of using a wheelchair, whether out of daily necessity, for enjoyment, for physical rehabilitation, or for strength or endurance conditioning.

Also within the scope of the present disclosure are aftermarket add-on devices configured in accordance with the joint movement-based control means presented herein, intended to be combined with a separate assistive propulsion device or system similar to those presently available on the market. In some embodiments, for example, such a system or device may be readily used in conjunction with other hybrid propulsion means, such as the motion-detection means implemented in devices such as the SmartDrive power-assist device by MaxMobility, disclosed in U.S. patent application Ser. Nos. 13/543,598 and 14/053,047, and in the e-Motion M15 add-on wheels by Alber, disclosed in U.S. Pat. No. 6,155,367.

In some embodiments, a system or device according to the present disclosure may be combined with other approaches at sensing and responding to wheelchair motion such as, for example, a deceleration-based hybrid propulsion function which detects and is responsive to the natural decay of momentum of the vehicle which follows each muscle-generated propulsive stroke enacted by the user. For example, upon sensing a predetermined minimum number of joint movement events, indicating vigorous propulsive effort by the user, the system begins providing assistive motor output responsive to each instance of detecting substantial deceleration of the wheelchair via measurement of wheel rotation velocity using magnetic Hall sensors. A joint movement detection device in combination with a vehicle motion measurement system would thus serve to ensure the user-intentionality of any response and also the accuracy of timing and output amplitude of assistive motor power.

A system or device in accordance with the present disclosure may, alternatively, be implemented to blend a user's muscle-generated effort with a resistive electromotive output for slowing or stopping the wheelchair. Electromagnetic resistive means, well known in the art of exercise equipment and also in the art of regenerative braking for vehicles such as bicycles, may offer advantages useful for muscle conditioning, rehabilitation, or athletic training. For example, U.S. Pat. No. 5,656,001, "Eddy current trainer for bicycles or other exercise equipment," describes an eddy current brake for use with exercise training devices, such as bicycle, ski and rowing exercise devices, and which includes a nonmagnetic, electrically conductive disk that is rotatably mounted between one or more electromagnets. U.S. Pat. No. 6,724,165, "Regenerative braking system for an electric vehicle" discloses a regenerative braking system for an electric vehicle having front and rear wheels, and includes a drive wheel, an actuating device, a regenerative braking control circuit, and a power electronics circuit. The system applies a regenerative braking torque to the drive wheel when the rider commands regenerative braking, and the process sensors signal a drive wheel velocity greater than zero.

Implementations of the present invention may include means for slowing down the wheelchair in order to safely and comfortably descend a decline, such as a hill or a ramp; in this case, the system or device enables the user to continue to engage in the normal movement pattern as if traveling on a level surface, rather than having to apply a potentially uncomfortable and awkward braking force that may be especially taxing on the user's hands, arms, shoulders, and torso while using the wheelchair.

In an embodiment, such a system or device may be combined with an inclinometer or a gravity-detecting accelerometer for the purpose of measuring and responding to the slope of the ground surface being traversed. Embodiments may, further, respond to other vehicle dynamics such as speed and acceleration, as measured through the use of a forwardly-directed accelerometer or with magnetic Hall sensors adapted for measuring rotational velocity of one or more of the ground-contacting wheels. Combined measurements of vehicle inclination, velocity and acceleration may thus serve to provide the system with a comprehensive set of logic inputs for accurately responding to the situation presented by the path over which the user desires to travel.

Embodiments may include one of a variety of commonly available batteries, capacitors, or supercapacitors, or may include a combination thereof, for the purpose of storing sufficient electrical charge for a sufficient duration necessary for all control circuitry to operate correctly and reliably and to provide the power output to drive the motor. Said electrical charge may be needed continuously and for long durations by control circuitry and microprocessors, but may be needed only momentarily for the driving the motor; therefore different subsystems having different power requirements may utilize separate electrical charge storage means. Whereas a typical control circuit with a microprocessor requires a continuous supply of less than 12 volts direct current at less than 500 mA, a brushless direct current motor may momentarily utilize more than 36 volts direct current at over 10,000 mA (10 amperes).

In addition, it may be useful for different subsystems utilizing separate electrical charge storage means to also utilize separate electrical charging means. Charging the continuous electrical supply for a control circuit with a microprocessor may only be needed once per month, whereas the power requirements of a large brushless direct current motor may warrant daily charging using a separate charging port and a more robust transformer for converting household alternating current (AC) to direct current for charging batteries.

Alternatively, the system may include a regenerative charging means whereby the user's muscle-derived power output in propelling the vehicle captures a portion of the energy associated with vehicle motion and stores this energy in an onboard battery, capacitor, or supercapacitor with the intention of momentarily powering the drive motor at a later occasion. The user would, in this case, be encouraged to self-propel the vehicle, especially while traveling over smooth, flat, or downhill surfaces, in order to "store up" for periods during which traversing more difficult surfaces demands an electromotive power assist.

In a similar fashion, the system may be configured so that each muscle-derived power stroke sufficiently charges an onboard capacitor which may be discharged during a user-motivated counter-stroke, in which the user returns the exertive-arm back to a poised position for the next power stroke, resulting in a sequence of alternated user-motive power output and electromotive power output. In this case, the charging and discharging properties of a capacitor and associated electronic components are exploited to produce smooth, reliable and predictable power consumption and output to a motor. Some embodiments may, instead, utilize pulse width modulation (PWM) to control and regulate the electromotive power output by utilizing an integrated logic circuit or a digital programmable microcontroller with the intention of simulating at least some aspects of the behavior of a purely analog control circuit.

Wireless signal transmission is accomplished by integrating a radio frequency transmitter within an electronics enclosure connected to the joint-movement sensor and is configured for optimal transmission over the distance from the user's arm to a receiver integrated within a second electronics enclosure. The second electronics enclosure is preferably mounted to the frame or upholstery of the wheelchair at an innocuous though serviceable location, such as suspended beneath the user's seat, clamped to a lateral frame member, or clamped to the rear drive axle of the wheelchair. Alternatively, the receiver may be integrated within a discrete motor unit which houses the motor and all circuitry necessary for energizing the motor as well as for responding to remote control signals. The transmitter, in response to logical input from a microprocessor, integrated circuit, or a much simpler discrete circuit, sends an appropriate activation or deactivation control signal to the receiver integrated within the vehicle-mounted enclosure. Radio communications technology, such as that utilized in garage door openers over the 315 MHz frequency band or, instead, Bluetooth or similar technology utilizing UHF radio waves in the ISM band of frequencies ranging from 2.4 to 2.485 GHz, may be employed for the purpose just described.

In some embodiments, it may be useful to enable a user to manually switch or transition between or among different operation modes, such as from a mode which is responsive to a user's movements as a result of his or her arbitrary, personal whim to a mode which is responsive to a synchronous pattern or sequence of events which must be performed in order to effectuate a control function such as propelling the vehicle forward. Manual switching or transitioning between or among different operation modes may be accomplished, for example, by way of a mechanical toggle switch, a momentary push-button switch associated with a logic circuit, or a sensor configured so as to accurately and reliably signal to the controller or to the system in general that the user has willed to transition to a different mode of operation.

In some embodiments, it may be preferable to relieve a user of the task of switching between or among different operation modes; this may be achieved by a system which automatically switches or transitions from one mode to another mode. Automatic switching or transitioning may be accomplished, for example, by way of an integrated logic circuit or a programmable microcontroller which, in response to receiving a predetermined number of input pulses from a joint movement sensor, automatically places the system into an appropriate state according to a logical statement programmed into the microcontroller or predetermined as a result of the behavior of an integrated logic circuit configuration.

For safety, it is useful to include a feature which automatically determines user readiness for the purpose of initializing the system and ultimately for willfully energizing the assistive motor. Such a feature may be useful for an arbitrary mode based on the user's personal whim or, instead, for a pattern-based mode; in both cases the added layer of complexity for startup translates to increased overall awareness and intentionality by the user as he or she occupies the vehicle and chooses to utilize its on-board assistive electromotive capabilities. The foregoing advantages may be further enhanced by including a "hello world," "standby," or "ready" signal for alerting the user, whether with a beep, click, vocalization, or other audible and recognizable sound, or with a light flash, color change, or other distinctly visible signal. Tactile signaling may also be useful, such as with a vibratory motor or piezoelectric vibrator.

Preferably, the joint-worn device is equipped with fail-safe circuitry for preventing accidental signaling of motor energization in the event of either sensor short-circuiting or sensor breakage; this design consideration speaks to the broader requirement that all wireless electronic signal transmissions within the system are solely the result of user-intended exertive-arm joint movements occurring within a well-defined angular range. A fault-sensing comparator circuit, for example, prevents or halts activation of the motor control function in response to sensor resistivity values rising above or falling below predetermined threshold values. The circuit detects sensor failure due to shorting, such as by entrance of moisture into the elastic sensor covering and, in the reverse scenario, as a result of sensor breakage. Similar effects may be achieved by employing programming logic, in the case of a device having a microcontroller, to prevent accidental activation due to damage to the sensor.

Affording the user or a clinician at least limited capabilities of adjusting parameters for how the system automatically determines, responds to, and signals user-readiness is advantageous as well. It is useful to afford the user or clinician the capability of adjusting parameters for how the system automatically isolates a particular movement, set of movements, or opposing movements of a portion of an arm, including the amount of time delay imposed before the system is ready for use. Translation of user-intended arm movements into electromotive power output can be optimized, for example, by isolating two opposing wrist joint movements and excluding or filtering out any noise introduced by other movements naturally occurring during use of the wrist joint while propelling the vehicle.

It is useful for the user or a clinician or qualified technician to be able to alter the mechanical range over which a sensor, itself, senses user-intended movements. For example, in the case of a wrist flexion and extension responsive device, an incorporated bend sensor may be shortened, lengthened, repositioned, reversed, structurally reinforced, altered so as to change its flexibility, or otherwise mechanically altered so as to change how sensitively the sensor reacts to wrist movements. The same is true for virtually any of the other applications depicted herein, whereby a mechanical alteration of a user joint movement sensor changes how acutely or sensitively the sensor reacts to angular changes of the joint.

It is also useful for the a clinician or qualified technician to be able to alter the sensitivity of the sensor circuitry or associated logic control means, whether it be a purely analog circuit or a circuit having digital processing capabilities, whereby alteration of the electronics, such as by adjusting a simple rheostat or potentiometer, or computer-programmed logic associated with the sensor of a user arm movement changes how the controller, or the system in general, reacts to movements of the exertive-arm or portions thereof. Alternative embodiments are envisaged in which the system automatically adjusts its own sensitivity or range according to the user's kinematic profile or range of motion during practice, that is, during a test run or during actual everyday use of the device in conjunction with the wheelchair.

DETAILED DESCRIPTION OF THE DRAWINGS

Figure 1A:
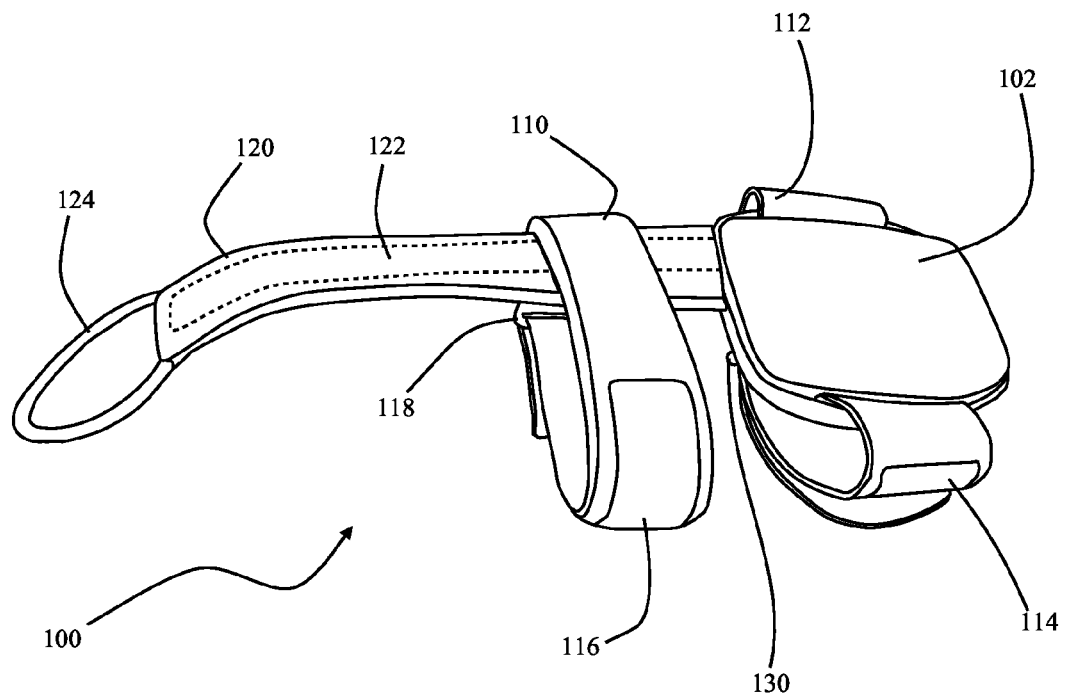
FIGS. 1A-D show various depictions of a wrist-worn joint-movement detection device as both a standalone apparatus and in relation to protective outerwear worn over the hand.

FIG. 1A depicts a wrist-worn movement detection device 100 having an electronics enclosure 102, a flexion-extension sensor 122, a sensor covering 120, a forearm strap 112, a wrist strap 110, and a finger loop 124. Securing the wrist-worn movement detection device 100 to a user's hand, wrist and forearm is accomplished by the user first inserting the middle and ring fingers through the finger loop 124, fastening the forearm strap 112 using Velcro fastener 114, and fastening the wrist strap 110 using opposing Velcro fastener 116. Wrist strap adjustment loop 118 is visible in FIG. 1A. LED indicator light 130 illuminates while an activating signal is transmitted from the transmitter contained within the electronics enclosure 110.

Figure 1B:
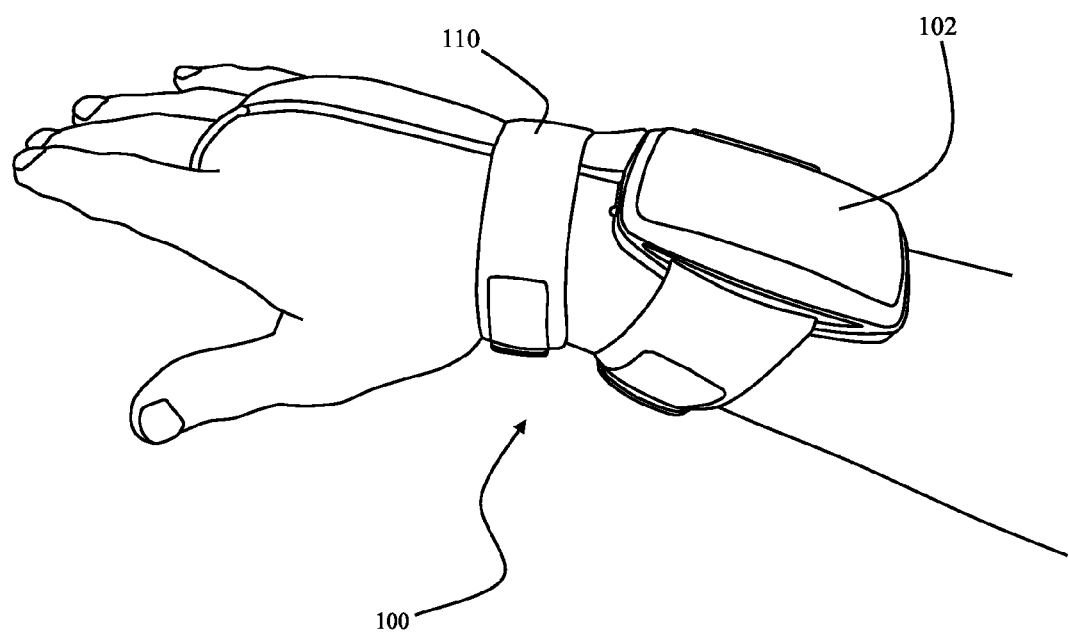

FIG. 1B depicts the wrist-worn movement sensor device which detects angular changes occurring in an isolated region near the wrist joint, specifically where the wrist strap 110 intersects the path of the flexion-extension sensor 122 of FIG. 1A (not visible in FIG. 1B) as it projects from the electronics enclosure 102 out towards the fingers. User-intended wrist movements, especially flexion, extension, radial deviation and ulnar deviation result in changes in the geometry of the sensor, which in turn produces changes in electrical resistance. Circuitry for detecting changes in the electrical resistance of the sensor is contained inside the enclosure 102, and includes failsafe means for preventing unwanted or accidental signaling to a vehicle-mounted controller, especially in the event of sensor failure. Sensor failure may include an event such as breakage of the sensor or shorting of the sensor, whether the result of normal wear-and-tear, misuse, physical damage, or water exposure.

LED indicator light 130 is useful for the purpose of making adjustments to the range over which user wrist movements switch between a state of activation and a state of deactivation. The indicator light 130 illuminates when the user's wrist is flexed or extended beyond a predetermined activation position, to indicate that the wireless transmitter contained inside the electronics enclosure 102 is transmitting an activation signal to a vehicle mounted controller.

When the user flexes or extends the wrist beyond a predetermined deactivation position, the indicator light 130 turns off, which indicates that the wireless transmitter contained inside the electronics enclosure 102 is no longer transmitting an activation signal.

A user, clinician, or a technician may make adjustments to the sensitivity of the sensor in opposing directions by opening the electronics enclosure and turning one or more adjustable "trim" potentiometers clockwise or counterclockwise. A window comparator circuit comprising a dual op amp (or dual comparator) integrated circuit may be useful for achieving this effect, employing a sensitivity adjustment feature as well as a hysteresis (positive feedback) adjustment feature to enable bi-directional sensor sensitivity control.

Instead of utilizing op amp- or comparator-type integrated circuitry, it may be preferred to adjust sensitivity by changing parameters within a logical code programmed onto a programmable logic microcontroller contained inside the electronics enclosure 102.

In either case, separation between a position of activation and a position of deactivation may be increased, for example, by decreasing sensor sensitivity (to activate) with respect to a first direction and also decreasing sensitivity (to deactivate) with respect to a second, opposing direction. Conversely, the separation between the two positions may be decreased, for example, by increasing sensor sensitivity with respect to a first direction (to activate) and also increasing sensitivity (to deactivate) with respect to a second, opposing direction.

In a similar fashion, the activation and deactivation positions may be adjusted to usefully change the sensitivity to changes in angular positioning produced by the user as he or she engages in a movement pattern, such as grasping the pushrim of a wheelchair and thrusting the arm forward in an arcing motion, along with flexion of the wrist. Afterwards, the arm is pulled back, the user's grip is relaxed, and the wrist is extended. Engaging in such a movement pattern thereby causes the angular positioning of the wrist to change. It is useful for a user, clinician or technician to be able to adjust how sensitively the wrist-worn movement detection device 100 responds to wrist flexion and extension movements. In essence, the wrist-worn movement sensor device may thus act as a switch having limits that may be very precisely adjusted according to the unique needs of the individual using the device.

Figure 1C:
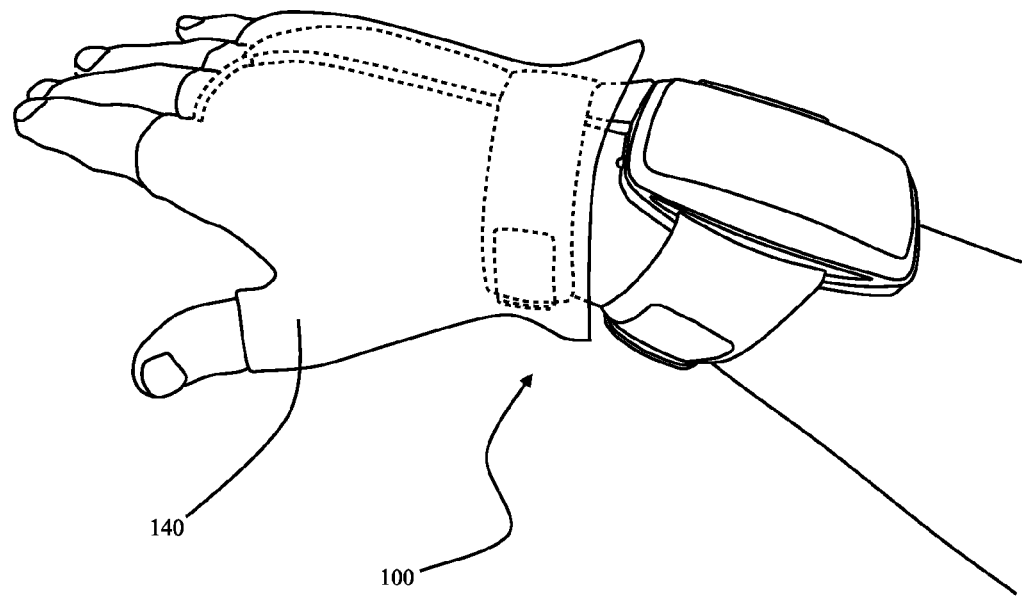
Figure 1D:
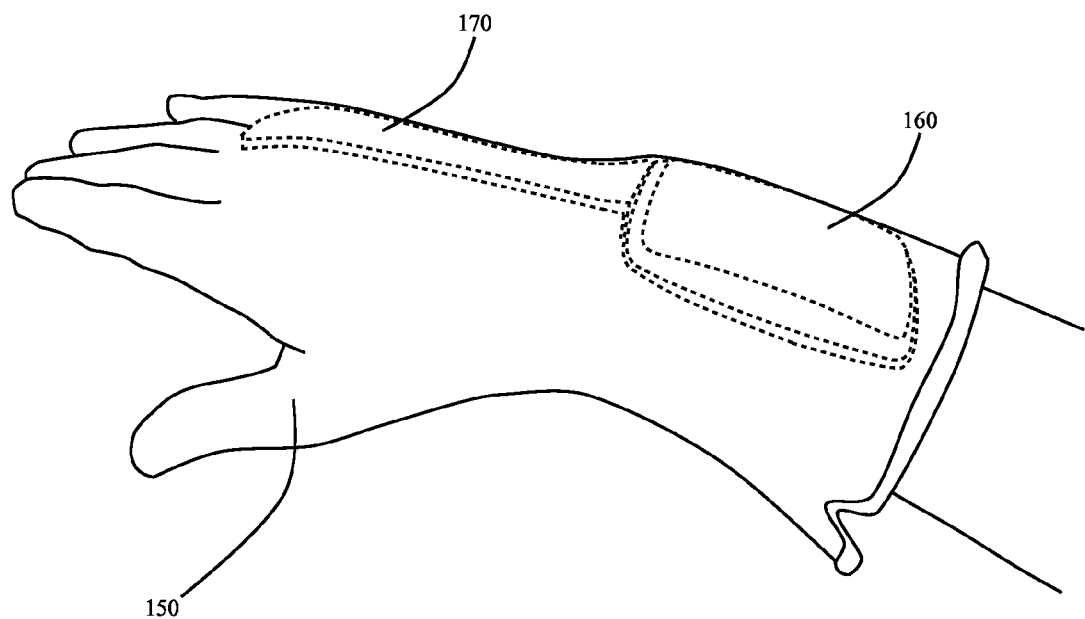

In FIG. 1C, the wrist-worn movement detection device 100 is shown, as worn by a user, beneath a glove 140 which serves to enhance the user's grip while also protecting the user's hand from dirt, debris, and abrasion during normal wheelchair use. The glove may, likewise, serve to protect the wrist-worn movement detection device 100 and may also help maintain the optimal position of the device 100 against the user's wrist. FIG. 1D depicts the wrist-worn movement detection device 100 in an integrated form with a glove 150, wherein the device 100 is glued, sewn, or otherwise secured at an optimal location within the glove, in which case achieving correct placement of the movement detection device 100 is greatly simplified—the user simply slips the glove over the hand to dispose the secured enclosure 160 and the secured flexion-extension sensor 170 in their intended locations relative to the user's hand, wrist, and forearm.

Figure 2A:
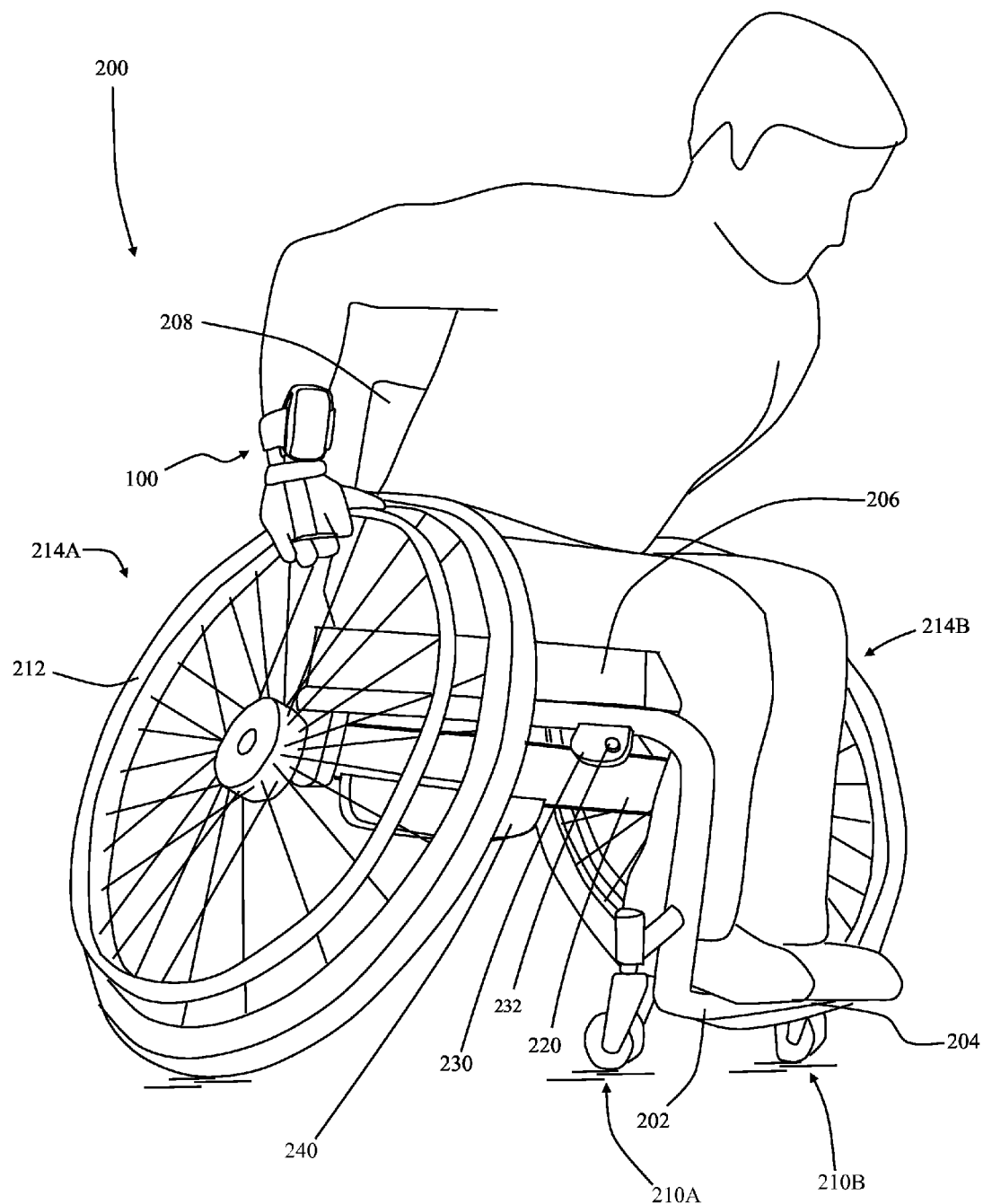
FIG. 2A shows a wheelchair occupant wearing a wrist-worn joint-movement detection device while engaging in propulsion of a wheelchair comprising a motorized axle-motor unit which drives the rear wheels of the wheelchair.

FIG. 2A depicts a wheelchair user wearing a wrist-worn movement detection device 100. The wheelchair 200 comprises a structural frame 202, a foot support 202, a seat 206, a back support 208, opposing caster assemblies 210A and 210B, and opposing rear drive wheels 214A and 214B. The wheelchair 200 is equipped with an axle-motor unit 220 coupled to the drive wheels 214A and 214B, a controller 230, and an electrical power source 240. The user's arm is positioned rearward with his wrist in a fully extended position as he grips the pushrim 212. In the event the user feels it necessary to halt power to the controller 230, he may depress the power switch 232 disposed on the power switch box 230 attached to the wheelchair.

Figure 2B:
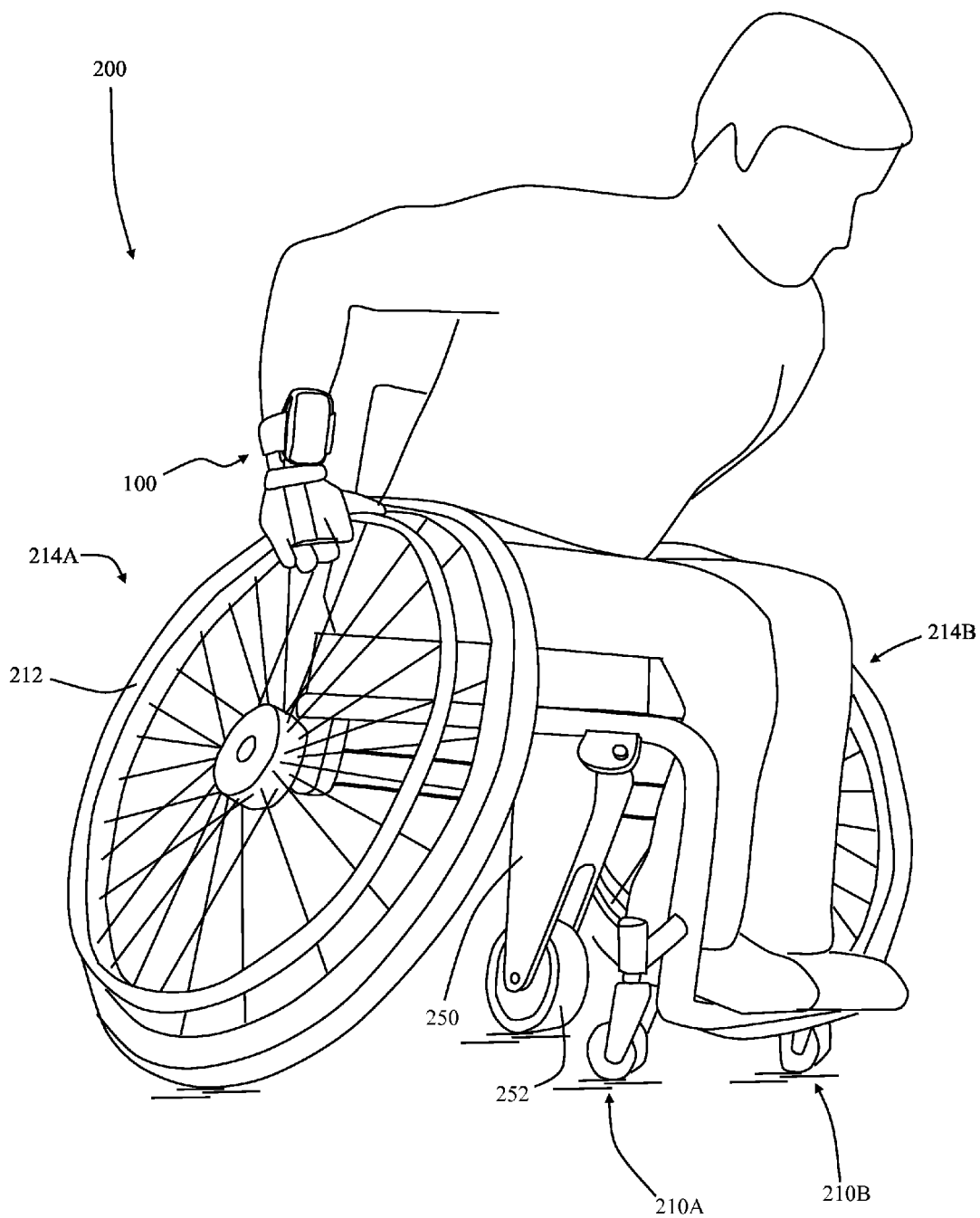
FIG. 2B shows a wheelchair occupant wearing a wrist-worn joint-movement detection device while engaging in propulsion of a wheelchair comprising an auxiliary wheeled motor unit mounted beneath the wheelchair and in contact with a ground surface.

The axle-motor unit 220 of FIG. 2A is replaced in FIG. 2B with an auxiliary wheeled motor unit 250 comprising controller electronics and motorized ground-contacting wheel 252.

Figure 3:
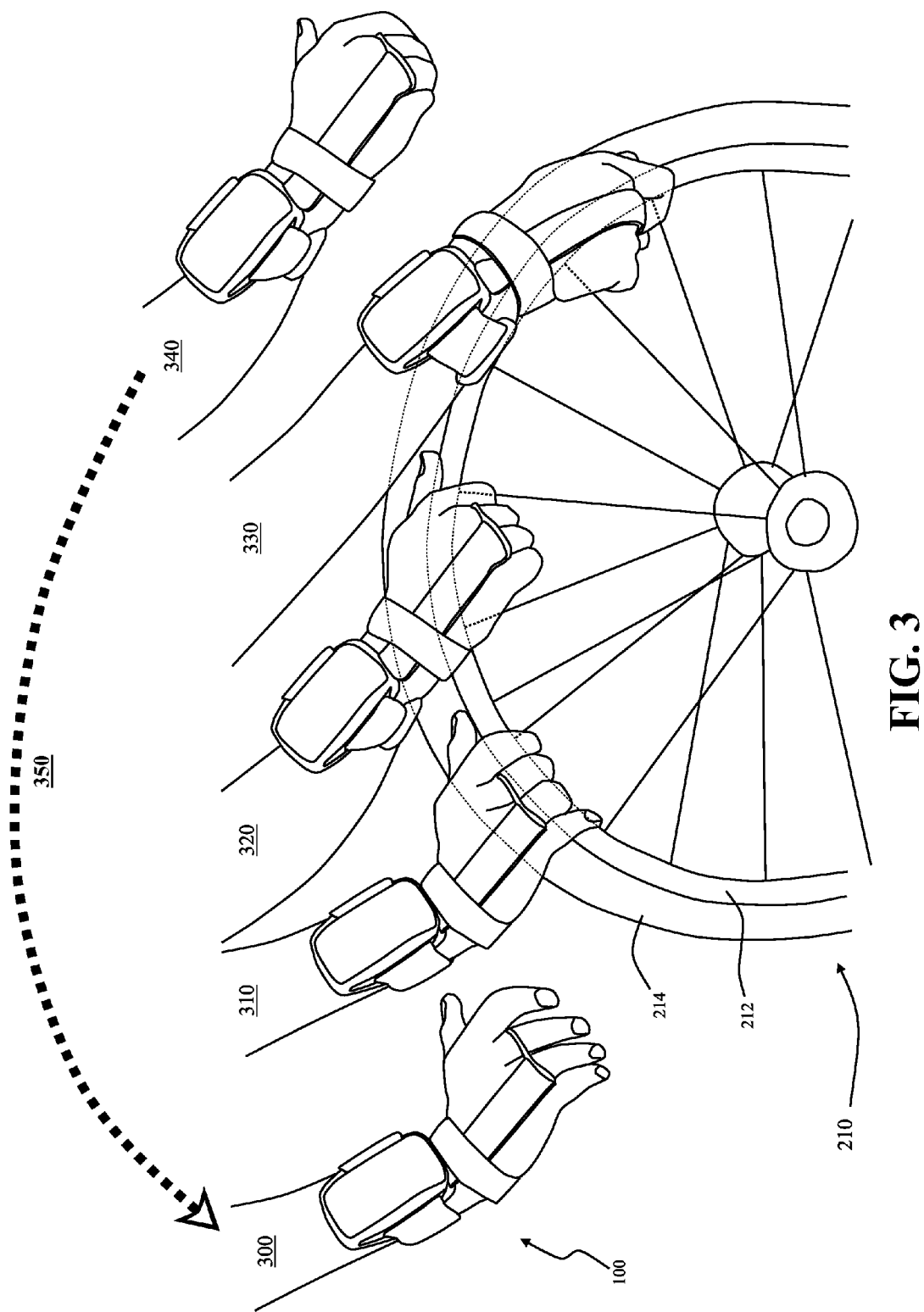
FIG. 3 depicts a sequence of arm, wrist, and hand positions assumed as a user engages in propelling the wheelchair in a forward direction, including the return of the arm, wrist, and hand to a rearward, pre-contact position.

FIG. 3 depicts pre-contact—300, rearward—310, middle—320, forward—330, and post-contact—340 positions of the wrist-worn movement sensor device 100 attached to the user's exerting arm as the user grips the pushrim 212 of the wheel 210 to motivate the wheelchair. The user may also, optionally, grip the tire 214 in order to achieve a stronger grasp over the wheel while exerting driving force thereagainst. Also depicted is the return path 350 as the user returns his hand, wrist, and forearm to the pre-contact position 300 from the post-contact position 340, enacted between each propulsive thrust against the pushrim 212.

As shown in FIG. 3, upon the user's hand contacting the pushrim 212 and, optionally, the tire 214, the user drives the wheel 210 in a forward direction, during which the wrist joint undergoes a transition from a substantially flexed joint angle at rearward-position 310, to a neutral joint angle at middle-position 320, to a substantially extended joint angle at forward-position 330. During the passage of the exerting-arm from the rearward-position through to the forward position, the user's hand follows an arcing path along the wheel; during propulsion to move about in the environment, the user repeats this transition in a very regular and predictable fashion, which serves as a basis for the pattern of joint movements readily exploited by the wrist-worn detection device.

The user's ability to grip, drive, release or otherwise manipulate the wheel using muscle-generated force is uninfluenced by the wrist-worn movement sensor device 100 as the user intentionally propels, reverses, steers, or applies braking force to carefully and precisely control the speed and direction of the wheelchair. At the same time, activating and deactivating the electromotive assistive propulsion by changing wrist joint position is co-incidental, though not accidental, with the user's intentional actions to control the speed and direction of the wheelchair. Effectuation of electromotive control functions, such as activation and deactivation of an assistive propulsive motor, may therefore be carried out synchronously with the application and transfer of muscle-generated forces to drive the wheel.

Furthermore, the user has the ability to flex and extend the wrist of the exertive-arm while releasing the hand from contact with the wheel, and so in some embodiments he or she may activate or deactivate the electromotive assistive propulsion in an arbitrary manner, that is, according to personal whim or desire to be relieved of the application and transfer of muscle-generated forces to the drive wheel.

Figure 4:
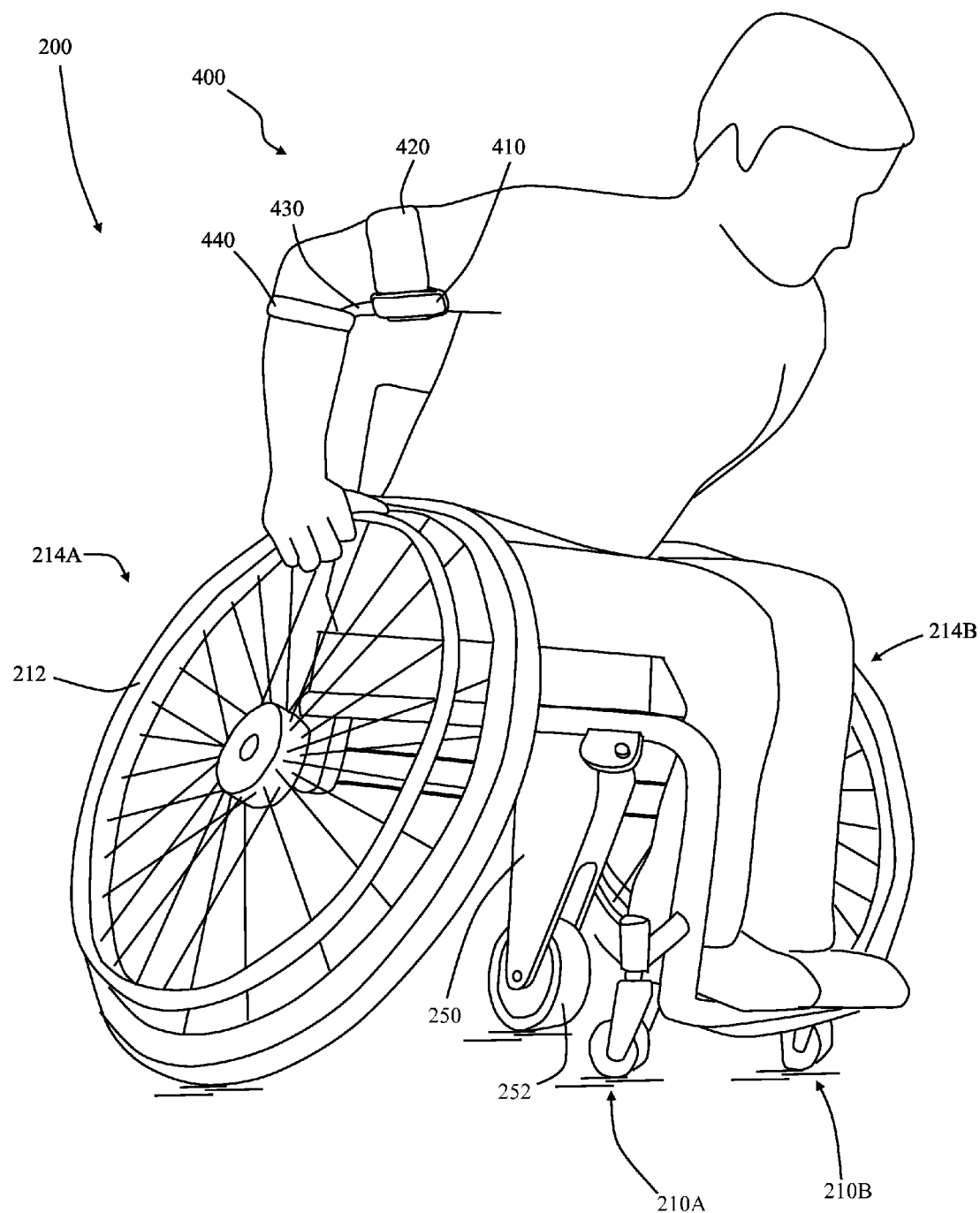
FIG. 4 shows a wheelchair occupant wearing an elbow-worn joint-movement detection device while engaging in propulsion of a wheelchair comprising an auxiliary wheeled motor unit mounted beneath the wheelchair and in contact with a ground surface.

FIG. 4 depicts a user wearing an elbow-worn joint-movement detection device 400 having electronics enclosure 410, upper arm strap 420, flexion-extension sensor 430, and lower arm strap 440. In this case, user-intended angular changes occurring about the elbow joint due to flexion and extension of the arm, cause momentary physical deformation of the sensor, which in turn produces readily detectable changes in electrical resistivity thereof; these changes are processed and signaled to the auxiliary motor unit 250 in the same way as described in the preceding figures.

Figure 5:
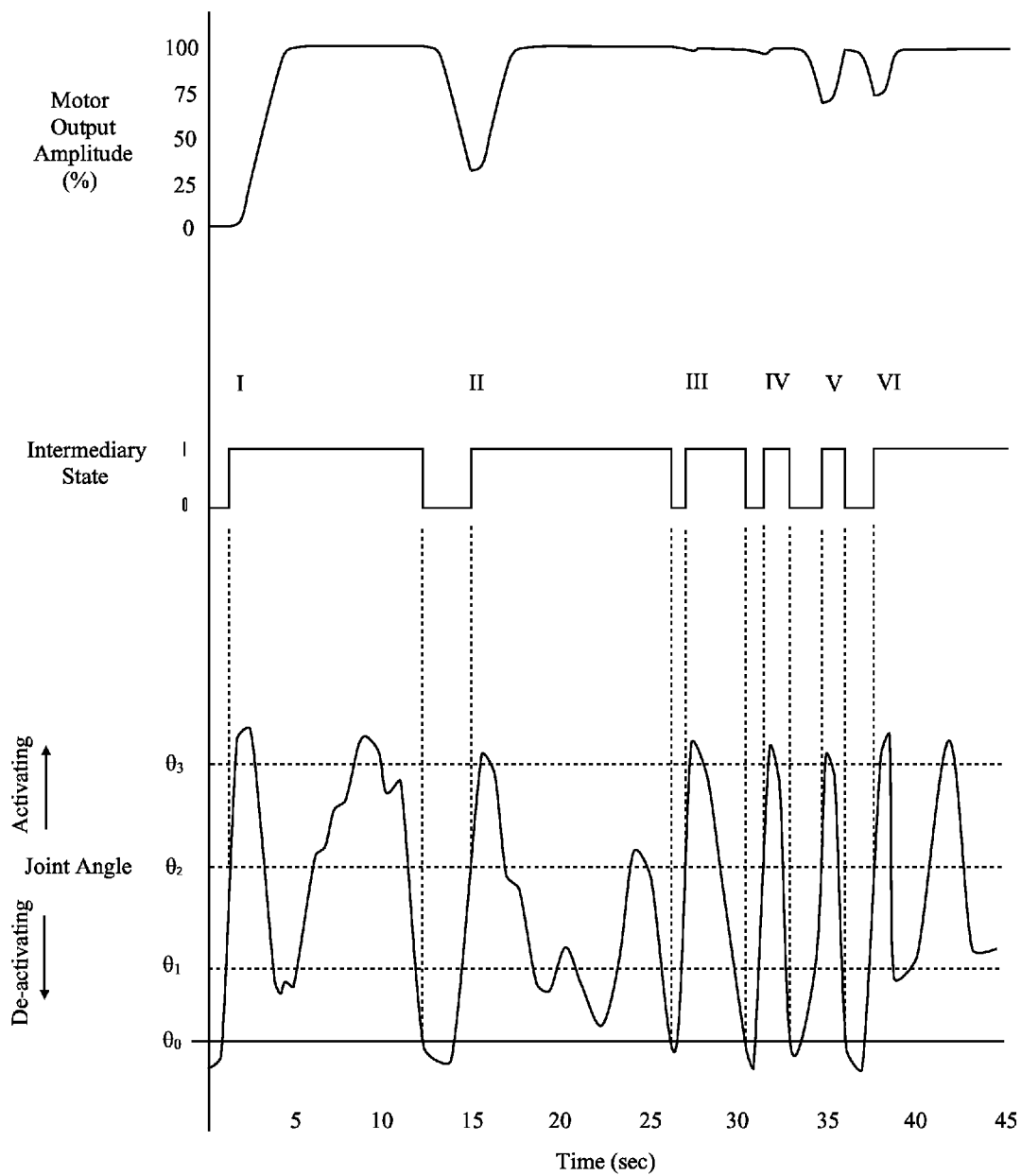
FIGS. 5, 6, and 7 show plots of a user's joint angle θ, over a 45-second timeframe in relation to the logical state (the "intermediary state") of an intermediary digital logic gate or microcontroller as well as the resultant motor output amplitude (expressed in percent of maximum allowed output) over the same timeframe.

FIG. 5 contains three separate line graphs, projected over the same window of time, depicting a relationship among input, intermediary, and output events. At the bottom of FIG. 5 is a graph showing angular fluctuation, over a 45-second timeframe, of a joint of an exertive-arm. An upper threshold is defined by an angle of activation, $\theta_2$, and a lower threshold is defined by an angle of de-activation, $\theta_0$. The angular or rotational difference between $\theta_2$ and $\theta_0$ thus defines an angular range of separation which imposes a buffering or filtering effect, wherein the joint angle must undergo a substantial change in the forward or activating direction so that it traverses $\theta_2$ in order to activate the control function and, upon the joint angle traversing $\theta_2$ to activate the control function, the joint angle must undergo a substantial change in the reverse direction to traverse $\theta_0$ in order to de-activate the control function. In some embodiments, a useful angular range separation may be about at least two degrees between $\theta_2$ and $\theta_0$, whereas in other embodiments, a range of about at least three degrees, five degrees, or ten degrees may be more suitable depending on the needs and abilities of the user as well as goals set with a clinician.

Depending on how the sensor is oriented or "flipped" within the sensor covering, activation will occur either during extension of the joint or during flexion of the joint; in either case, the angle of activation, $\theta_2$, must be traversed in order to effectuate an intermediary logic state change from 0 to 1. Likewise, the angle of de-activation, $\theta_0$, must be traversed in order to effectuate an intermediary logic state change from 1 to 0. Thus, as the joint of the user's exertive-arm undergoes angular changes during navigation of the wheelchair by the user, switching events occur at the upper and lower thresholds of the angular range of separation. Furthermore, when the intermediary logic state is 0, the intermediary logic state remains 0 and changes to 1 if and only if the joint angle traverses the angle of activation, $\theta_2$. When the intermediary logic state is 1, the intermediary logic state remains 1 and changes to 0 if the joint angle traverses the angle of de-activation, $\theta_0$ or if the fail-safe circuitry detects sensor damage due to a breakage or a short circuit.

The intermediary circuit or program responds to state changes by outputting clean, distinct HIGH and LOW output values, thus filtering out noise generated during transduction of joint movement, via the resistive sensor, into the analog input signal, helping to ensure user intentionality. As the user engages in propulsion, assuming the angles of activation and de-activation are properly adjusted, the natural movements of the user's exertive-arm effortlessly enact switching of the intermediary logic state. With practice, the user consciously attends to the speed of his or her exertive-arm movements and the duration of activation and deactivation instances and need not be preoccupied with how far the joint is flexed or extended as this is automatically gauged by the device; the user is thus enabled to focus on the overall speed and direction of the wheelchair.

Dotted vertical lines show the relationship between joint angle change events and intermediary state change events. Instances I, II, III, IV, V, and VI, shown above the plot of the intermediary state of the system, indicate moments of transition of the intermediary state from 0 to 1.

The resultant logic output from the intermediary processing circuitry is further translated, via a motor controller circuit, into an appropriate percentage of total motor output amplitude, plotted at the top of FIG. 5. A fixed rate of output amplitude increase and decrease is seen in the slope of the line, and smooth ramp-up and ramp-down curves are seen at instances of activation and de-activation; these features are shown merely as examples, as other useful configurations may utilize variable rates of output amplitude increase or decrease as well as sharper or more gradual ramp-up and ramp-down curves. A variable rate of amplitude increase may furthermore be a function of vehicle speed as sensed via magnetic Hall sensors integrated within a ground-contacting wheel or may be a function of vehicle inclination as sensed via an inclinometer mounted to the wheelchair.

Figure 6:
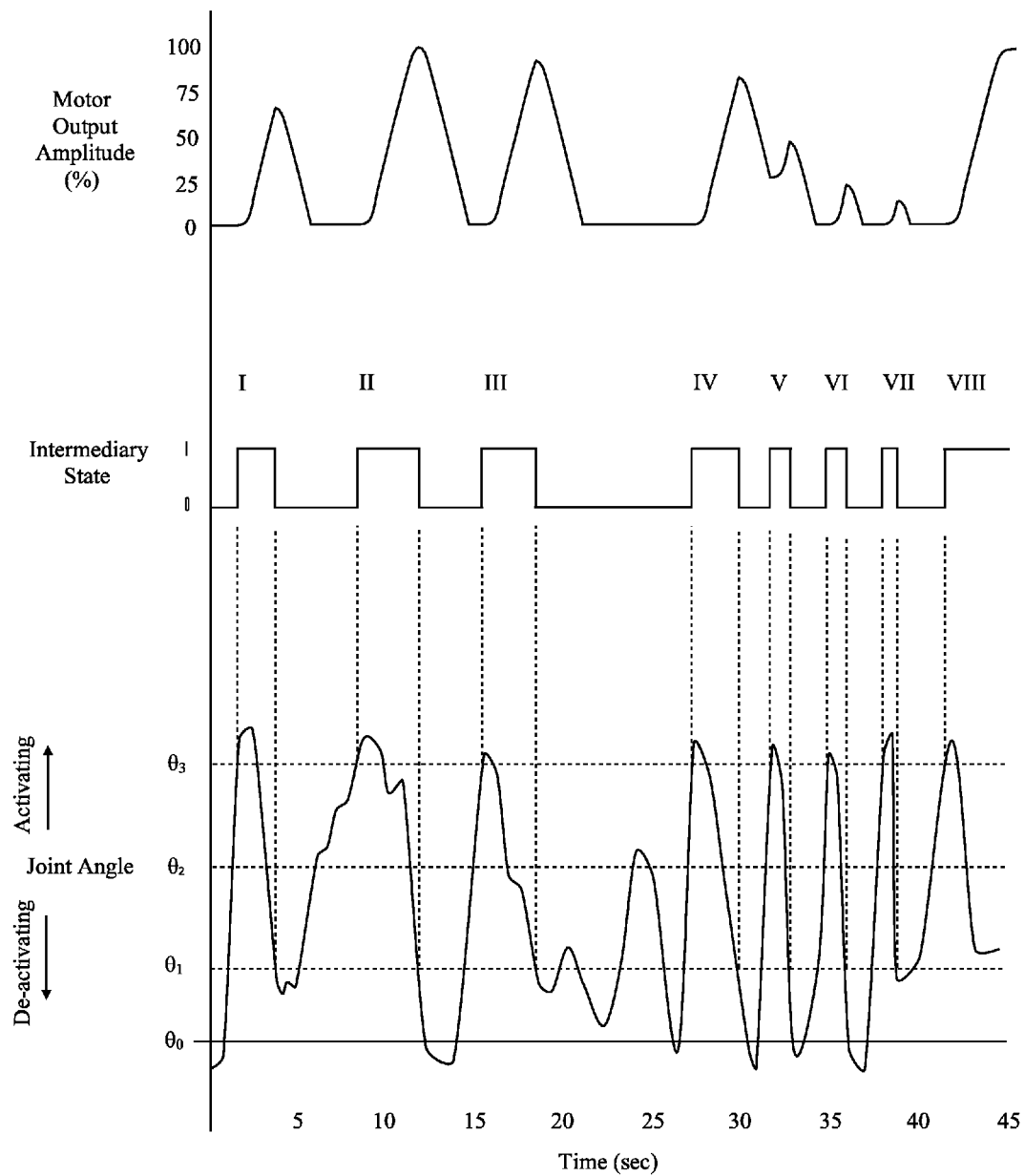

In FIG. 6 a set of line graphs, similar to those in FIG. 5, depicts an alternate hypothetical relationship among input, intermediary, and output events occurring over the same window of time, in which the angle of activation is $\theta_3$ and the angle of de-activation is $\theta_1$, thus utilizing a substantially different angular range of separation. Given an identical plot of joint angle fluctuation over the same timeframe, dramatically different motor output amplitude results are produced. In other words, FIG. 6 depicts the behavior of a system having the same electronic functions or microcontroller programming as in FIG. 5, except that it employs different upper and lower resistivity threshold values. In FIG. 5, motor output is sustained at its maximum allowed amplitude with only three substantial instances of deactivation, whereas in FIG. 6, a more intermittent, pulsing output is achieved, swinging rapidly between minimum and maximum allowed motor output amplitudes.

Figure 7:
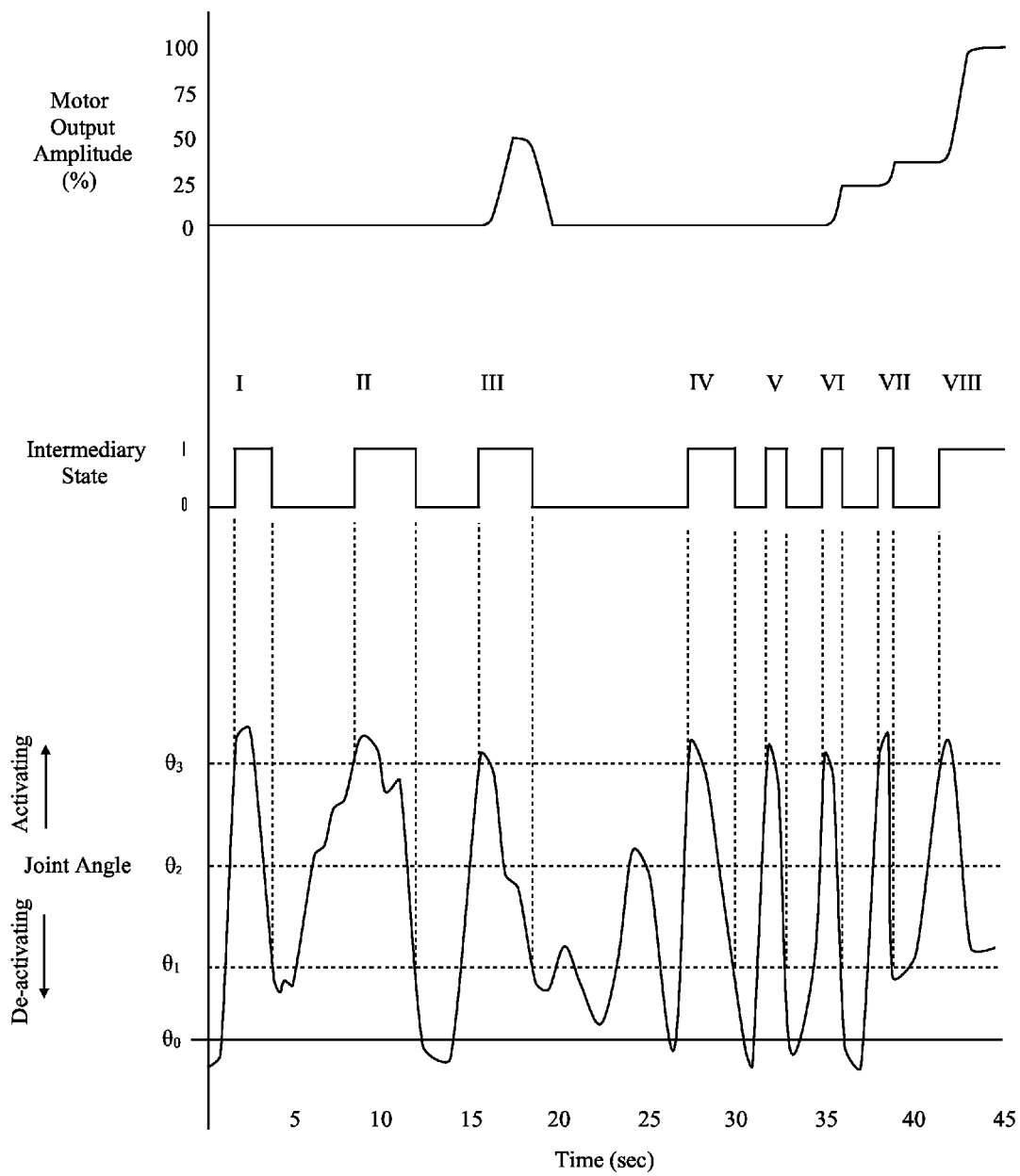

FIG. 7 depicts an alternate hypothetical relationship among input, intermediary, and output events occurring over the same window of time, showing the behavior of a system comprising a substantially different electronic or programming functionality compared with FIGS. 5 and 6. Although responsive to the same angles of activation and de-activation as in FIG. 6 to produce an identical plot of intermediary state values, in this case further automatic "decision-making" follows: three consecutive intermediary state transitions from 0 to 1, each having a maximum separation time of 7 seconds, allow up to 50% motor energization upon the third activation instance. Also, subsequent activation instances result in additional, cumulative motor energization for each instance, up to 100%, unless de-activation lasts more than 7 seconds, at which point the program resets and awaits another series of three consecutive intermediary state transitions from 0 to 1.

As can be seen in the plot of motor output amplitude at the top of FIG. 7, the rate of output amplitude increase is fixed in this example, so the resultant motor output may not reach the maximum allowed value if activation is not maintained for a sufficient duration. In other words, the output amplitude is a function of the duration of time over which the device is maintained by the user in the activated state before enacting a transition therefrom. Also, a deactivation period lasting more than 7 seconds "resets" the program and again waits for three consecutive 0 to 1 transitions. Beginning at activation instance VI, rapid "bursts" of activation, indicative of vigorous propulsive muscle-generated effort by the user, are followed by short de-activation periods, resulting in a cumulative-increase effect, in this case all the way up to 100% allowed motor output amplitude.

Example I

A wrist-worn device was created to detect changes in wrist joint angle during use of a manually-propelled wheelchair. The device comprises an electronics enclosure made of black ABS plastic which, upon fastening using a 1.5 inch wide elastic forearm strap, lies comfortably against the back of the user's forearm. A flexion-extension sensor, measuring approximately 4 inches in length and 0.375 inches in width, protrudes from the electronics enclosure along the back surface of the hand towards the ring finger. The sensor is sandwiched between two plastic sheaths to provide rigidity to protect the sensor from damage due to extreme bending and also to "smooth out" sensor responses to changes in wrist angle. The thickness of the sensor and sheaths is approximately 0.1875 inches. A 1-inch wide elastic sensor covering surrounds the sandwiched sensor, with a resultant thickness of about 0.25 inches. Sewn perpendicularly to the sensor covering, about 0.75 inches from the electronics enclosure, is a 1-inch wide wrist strap. A circular elastic finger loop having a diameter of about 1.5 inches is sewn to the end of the elastic sensor covering. The device is attached to the user's hand, wrist, and forearm by first inserting the middle and ring fingers through the circular elastic finger loop and then fastening the elastic forearm strap around the forearm using a loop and a Velcro fastener, and last by fastening the wrist strap around the wrist using a loop and a Velcro fastener.

On the outside of the electronics enclosure are a power switch, an LED activation indicator, and a micro-USB battery charging jack. Contained within the electronics enclosure is a 3.7 volt lithium ion battery and circuit board containing the circuitry responsible for interpreting wrist sensor resistance values as well a signal transmitter section for transmitting a radio signal to a receiver and motor controller located beneath the wheelchair seat.

The circuit consists of a single-supply dual operational amplifier ("op-amp") contained within an 8-pin dual in-line package (DIP) or surface mount (SM) integrated circuit chip. The first half of the dual op-amp is configured as a switching comparator having a Schmitt trigger for the purpose enabling clean, jitter-free switching between an activated state and a de-activated state. The second half of the dual op-amp is configured to respond to sensor short-circuit type failure.

Initially, the inverting input voltage of the switching comparator is about 2.0V and a non-inverting reference voltage is set, using two resistors as a voltage divider, at 1.82V Upon flexion of the wrist beyond an "activating angle" (and therefore, flexing of the resistive sensor) of about 15 degrees, the sensor is bent to a corresponding degree; as the resistance of the sensor falls, the inverting input voltage of the switching comparator drops below the non-inverting reference voltage (1.82V) to about 1.70V, thereby triggering the switching comparator output to HIGH to activate the transmitter, in turn wirelessly signaling the controller to energize the vehicle-mounted motor. The LED activation indicator illuminates upon the switching comparator output changing to HIGH. Incorporation of a potentiometer into the voltage divider enables adjustment of the reference voltage greater or less than 1.82V, and thus adjustment of the activating angle by a user, technician or clinician.

By virtue of the Schmitt trigger configuration, upon triggering the switching comparator to output HIGH, the reference voltage at the non-inverting input is increased from 1.82V to 2.45V; thus in order to change the state of the switching comparator from HIGH to LOW, the sensor resistance must be returned to a value substantially greater than it was prior to initiating the output of the switching comparator to change from LOW to HIGH.

In order to deactivate the signal transmitter and thus de-energize the vehicle-mounted motor, the wrist must be returned in the opposite direction, that is, by wrist extension, to a "deactivating angle" of about 5 degrees. In this example, upon achieving the deactivating angle, the inverting input of the switching comparator exceeds 2.45 V, triggering the output of the switching comparator to change from HIGH to LOW. The LED activation indicator turns off upon the switching comparator output changing to LOW.

An angular separation of about 10 degrees thus exists between the activating angle and the deactivating angle, which results from the hysteresis effect created by the switching comparator and Schmitt trigger, described above. The resultant electrical positive-feedback "lag" serves to filter out "noise" created by smaller, insignificant changes in the sensor resistance and enhances the intentionality of the switching action of the wrist-worn device, that is—to ensure that the wireless signaling to energize and de-energize the vehicle-mounted motor occurs smoothly and harmoniously along with the user's efforts to manually propel the wheelchair. A transistor and a potentiometer incorporated with the Schmitt trigger enable adjustment of the resultant reference voltage increase so that it may be greater or less than 2.45V, enabling adjustment of the deactivating angle; by utilizing the hysteresis adjustment together with the aforementioned adjustability of the activating angle, a user, technician, or clinician may effectively increase or decrease the angular separation between the activating angle and the deactivating angle as well as precisely adjust the degree of wrist flexion required to achieve both angles, keeping in mind the mobility and comfort of the user's wrist.

The device is also equipped with fail-safe circuitry to prevent accidental signaling of motor energization in the event of either sensor short-circuiting or sensor breakage; this design consideration speaks to the broader requirement that all wireless electronic signal transmissions are solely the result of user-intended wrist joint movements occurring within a well-defined angular range. The second half of the dual op-amp is configured as a fault-sensing comparator having a non-inverting reference voltage of about 1.32V, configured to respond to any sensor failure occurring as a result of shorting, such as by entrance of moisture into the elastic sensor covering. A short circuit across the sensor will result in a large decrease in sensor resistance and will cause the inverting input voltage to drop below the non-inverting reference voltage (1.32V); in such an event, the fault-sensing comparator will output HIGH, in turn causing an NPN transistor to pull the non-inverting input of the switching comparator to ground, thereby ensuring the switching comparator output will become and remain LOW. On the other hand, sensor breakage may also occur, which will cause a large increase in sensor resistance. As a result, the inverting voltage of the switching comparator will rise substantially higher than the non-inverting reference voltage (1.82V during the LOW state and 2.45V during the HIGH "hysteresis" state), thereby ensuring the switching comparator output will become and remain LOW.

During each manual propulsion event in which the user grasps at least one of the two opposing pushrims connected laterally to the opposing rear drive wheels of the wheelchair, the user's wrist joint cycles through a pattern of complex movements or a "stroke." The device has been configured to respond primarily to wrist flexion and, to a lesser degree, radial deviation, both which occur as the user grasps the pushrim and applies forward propulsive force thereagainst. The device is also responsive to the opposite movements as the user returns his or her hand from a forward position, following a forward thrust, to a rearward position prior to beginning the next forward thrust; this is accomplished by a continuous wrist action involving both radial extension and ulnar deviation. All of the aforementioned wrist movements occur primarily at the user's radiocarpal joint and the midcarpal joint; the wrist-worn apparatus remains unresponsive to pronation and supination movements of the hand and forearm, thus serving to discriminate against movements which do not correlate with actions taken by the user specifically for manual propulsion. With each propulsive stroke, the motor becomes energized during the propulsive portion of the stroke, and then becomes and remains de-energized in the non-propulsive portion of the stroke during which the user returns his or her exertive-arm in the rearward direction.

In an event that the user wishes to immediately halt motor propulsion, he or she depresses a momentary push-button style "kill switch," mounted on the side of the wheelchair frame and within easy reach from an upright seated position. In addition, the amplitude of motor energization may be quickly adjusted by turning a knob affixed to a rotary potentiometer, also mounted to the side of the wheelchair frame, thus serving as a simple and readily accessible speed control.

Example II

A wrist-worn device is comprises structural and electronic elements identical to those described in Example 1, but is instead configured having the flexion-extension sensor flipped over—that is, rotated 180 degrees about its lengthwise axis. Compared against Example 1, the action of the device is thus reversed so that motor energization is activated upon the wrist being extended beyond an activation angle, during the return of the user's hand from a forwardmost position on the pushrim of the wheel to a rearwardmost position. Motor energization is deactivated upon wrist movement, in the opposite direction, beyond a deactivation angle. Similar to the electronic circuitry described in Example 1, an angular separation occurs due to a hysteresis effect created by a switching comparator and a Schmitt trigger, so that a range of separation exists between the activation angle and the deactivation angle, thereby enabling smooth modulation of the user's muscle-generated propulsive effort with countercurrent motorized propulsion. In other words, in this example the motor becomes and remains energized during the non-propulsive portion of the user's propulsion stroke during which the user returns his or her exertive-arm in the rearward direction. With each propulsive stroke, the motor becomes energized in the non-propulsive portion of the stroke during which the user returns his or her exertive-arm in the rearward direction, and then becomes and remains de-energized during the propulsive portion of the stroke.

Example III

Rather than comprising an op-amp integrated circuit, a wrist-worn device comprising structural elements identical to those described in Example 1 utilizes a programmable logic microcontroller for interpreting input received from the flexion-extension sensor. Said input is processed within the wrist-worn device enclosure and is wirelessly communicated to a motor controller mounted beneath the wheelchair seat. In order to more smoothly and appropriately modulate motor energization with muscle-derived propulsive effort, additional control is implemented locally with the motor controller, including interfaces with speed sensors and an incline sensor, an on-board programmable microcontroller, as well as including additional circuitry for smoothly "ramping" motor energization up and down.

The system is responsive to repetitions of joint movements, in that at least three activation-to-deactivation transitions are required within a 10-second timeframe before initially energizing the motor; this ensures motor energization is the result of the user willfully engaging in repeated arm movements to motivate the wheelchair in the forward direction, rather than motor energization occurring by mere happenstance.

By virtue of the programmability of both the microcontroller contained within the enclosure of the wrist-worn device and the microcontroller disposed locally to the motor controller, a user, technician, or clinician is afforded tremendous flexibility in configuring the sensitivity of the response to sensor input, the duration of activation signal transmission, whether the activation signal is transmitted during the propulsive portion of the manual push stroke or during the return portion of the manual push stroke, as well as the amplitude of motor energization and the duration of such motor output upon receiving an activation signal from the wrist-worn device.

In the present example, the amplitude of motor energization is varied as a function of the frequency of propulsive joint movements enacted by the user within a 5-second timeframe. If, after having achieved at least three activation-to-deactivation transitions within a 10-second window, the user enacts a single forward thrust movement within a 5-second window, the motor will be energized to provide 10% of its maximum propulsive output for 3 seconds. If, within a 5-second window, the user enacts two forward thrust movements (as he or she is working more rapidly to motivate the vehicle at a higher velocity), the motor will be energized to provide 25% output for 3 seconds. If, within a 5-second window, the user works very rapidly to enact three or more forward thrust movements, the motor will be energized to provide 50% output for 3 seconds.

Furthermore, all of these output values change depending on sensor measurements of the inclination of the wheelchair, such as the degree of uphill or downhill slope being encountered by the user along a trail or sidewalk. For example, if the user is traveling down a gradual incline and provides a single forward thrust in a 5-second window, the motor energizes only to 5%. In the opposite situation, if the user is traveling up a steep incline and provides three or more forward thrusts in a 5-second window, the motor energizes to over 90% of its maximum power output. In both cases, the user benefits from a level of assistive motor propulsion that is appropriate for the demands of the travelled pathway and, at the same time, the user is encouraged to self-motivate the wheelchair before experiencing the added boost of power to achieve higher and perhaps more exhilarating speeds.

The system is responsive to drastic downhill situations. First, the vehicle-mounted inclinometer detects a substantial downward force of gravity acting upon the wheelchair and then, upon the user flexing her wrists while exerting braking effort against the rear drive wheels, the system applies regenerative braking torque to the propulsive motor in order to safely, comfortably descend the incline. As a consequence, the system relieves the user of having to strain her shoulders, arms and hands as she normally would in order to apply the large amount of braking force needed to slow the wheelchair down to a safe and comfortable speed and to maintain overall control of the wheelchair.

The values specified within the programming logic may be modified by a user, technician or clinician using computer software or a mobile device application and may thus be used to implement a variety of user training "profiles," each based around achieving specific goals for purposes such as rehabilitation or rigorous strength conditioning, or instead to gently motivate a sedentary wheelchair user to become more physically active. The overarching objective, as embodied in the aforementioned examples, is to provide a safe and convenient means for a user of a wheelchair to enjoy the benefits of assistive motor propulsion while also achieving or maintaining a high level of strength, flexibility, and range of motion through healthfully engaging in body movement and muscle-generated propulsion.

It may, furthermore, be preferred to configure the system for the purpose of compensating for lateral strength imbalance between the user's exertive-arm and the opposite arm by associating exertive-arm joint movements with energization of a motorized wheel unit, secured beneath the wheelchair, which is disposed at a substantially offset location relative to the centerline of the wheelchair; this may be achieved, for example, by mounting the motorized wheel unit to a structural member of the wheelchair at a distance of at least about one inch and up to as much as about six inches from the centerline of the wheelchair. The resulting mechanical offset of the motorized wheel unit provides a useful training and rehabilitation means for a wheelchair user who has recently injured one arm or shoulder and who requires gentle encouragement to self-propel the wheelchair while experiencing a helpful magnitude of assistive motor propulsion biased towards the side of the injured arm or shoulder. As an alternative to resorting to a fully motorized "powerchair," the example above thus serves as a beneficial tool for a therapist or other clinician in helping a patient in the situation just described to regain function, strength, and independence.

Remarks

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above compositions, products, and methods without departing from the scope of aspects of the invention, it is intended that all matter contained in the above description shall be interpreted as illustrative and not in a limiting sense. Reference to particular illustrative embodiments should not be construed as limitations. The inventive devices, products, and methods can be adapted for other uses or provided in other forms not explicitly listed above, and can be modified in numerous ways within the spirit of the present disclosure. Thus, the present invention is not limited to the disclosed embodiments.

I claim:

1. A device responsive to movement of a joint of a user's exertive-arm during use of a manually-propelled wheelchair, the device configured for secure attachment over the joint, the device further configured to preserve the functioning of the user's exertive-arm during use of the manually-propelled wheelchair, the device further configured to remain free from contact with a grip surface of the wheelchair during propulsion, steering, and braking of the wheelchair along a desired course, the device comprising:
   a.) a sensor having electrical resistivity which varies as a result of mechanical deformation of the sensor;
   b.) a processor circuit configured for generating a control output in response to variation in electrical resistivity of the sensor;
   c.) an electronic communication means, responsive to the control output of the processor circuit, for sending a control signal to a motor energizing unit to effectuate a motor control function;
   wherein the device associates movement of the joint of the user's exertive-arm with energization of a motorized wheel assembly to assist the user in navigating the wheelchair along the desired course.

2. The device of claim 1, wherein the motor control function is activated upon a user's joint traversing an activating joint position by bending the joint in a first angular direction.

3. The device of claim 2, wherein the motor control function remains activated while the joint angle remains beyond a deactivating joint position, and wherein the motor propulsion control function becomes de-activated upon bending the joint in an opposing second angular direction to traverse the deactivating joint position.

4. The device of claim 3, wherein the activating joint position and the deactivating joint position define an angular range of separation over which the motor control function remains activated subsequent to bending the joint in the first angular direction to traverse the activating joint position.

5. The device of claim 4, wherein the angular range of separation between the activating joint position and the deactivating joint position is at least about two degrees.

6. The device of claim 4, wherein the angular range of separation is adjustable.

7. The device of claim 1, the sensor comprising an elastic portion having a variable length, wherein the electrical resistivity of the sensor is associated with the variable length of the elastic portion the sensor.

8. The device of claim 1, wherein the electrical resistivity of the sensor is associated with a measured amount of angular deviation of at least a portion of the sensor relative to a straight line passing lengthwise through the sensor.

9. The device of claim 1, further comprising a sensor-fault detection means, wherein an increase in electrical resistivity of the sensor above a predetermined maximum resistivity value prevents or halts activation of the motor control function and wherein a decrease in electrical resistivity of the sensor below a predetermined minimum resistivity value prevents or halts activation of the motor propulsion control function.

10. The device of claim 1, configured for secure attachment to at least a portion of the user's hand.

11. The device of claim 1, configured for secure attachment to at least a portion of the forearm of the exertive-arm.

12. The device of claim 1, adapted to be securely worn over the wrist joint of the exertive-arm.

13. The device of claim 1, adapted to be securely worn over the elbow joint of the exertive-arm.

14. A wheelchair motor control system, comprising:
   a. a motor unit comprising a motor and a motor controller, said motor configured for driving a ground-contacting wheel about a rotation axis of the wheel, said motor controller configured for drawing electrical current from an electrical power source, said motor controller further configured for regulating an output of electro-motive force, said motor unit configured for applying the output of electro-motive force against a structural member of the wheelchair for assisting a user while navigating the wheelchair along a desired course;
   b. means for effectuating a motor control function, said means being responsive to joint angle changes accompanying movement of a portion of a user's exertive-arm, said means comprising a sensor having electrical resistivity which varies as a result of mechanical deformation of the sensor during joint angle changes, said means further comprising a signaling means for transmitting a control signal to the motor unit;
   wherein the wheelchair motor control system coordinates the output of electro-motive force provided by the motor unit with movement of the portion of the user's exertive-arm during navigation of the wheelchair by the user.

15. The wheelchair motor control system of claim 14, the means for effectuating a motor control function configured for performing an intermediary operation which, in turn, transmits the control signal to the motor unit, said intermediary operation comprising a logical state transition between a first logical state and a second logical state, the system configured for responding to bending of the user's joint in an activating direction beyond an angle of activation wherein the system remains in the first logical state until a resistivity value of the resistive sensor traverses an activating threshold value, the system further configured for responding to bending of the user's joint in a deactivating direction beyond an angle of de-activation wherein the system remains in the second logical state until a resistivity value of the resistive sensor traverses a deactivating threshold value,
   wherein, while the system is in the first logical state, upon the resistivity value of the resistive sensor traversing the activating threshold value, the system is transitioned into the second logical state, and wherein, while the system is in the second logical state, upon the resistivity value of the resistive sensor traversing the deactivating threshold value, the system is transitioned into the first logical state.

16. The wheelchair motor control system of claim 15, wherein a substantial increase in resistivity of the resistive sensor above a maximum resistivity value prevents or halts activation of the motor control function, and wherein a substantial decrease in resistivity of the resistive sensor below a minimum resistivity value prevents or halts activation of the motor control function.

17. The wheelchair motor control system of claim 15, wherein the output amplitude is a function of a repetition, enacted by the user, of the device transitioning between the first logical state and the second logical state.

18. The wheelchair motor control system of claim 15, wherein the output amplitude is a function of a duration of time over which the device is maintained by the user in either the first logical state or the second logical state before enacting a transition therefrom.

19. The wheelchair motor control system of claim 15, wherein the output amplitude is a function of speed, acceleration, or inclination of the wheelchair.

20. A method of enabling coordination of assistive motor energization for a wheelchair with a user's exertive-arm movements during manual navigation of the wheelchair along a desired course, said method comprising:
 a. configuring a joint movement detection device for secure attachment to the user's exertive-arm and for detecting and responding to angular changes of a joint of the user's exertive-arm during manual navigation of the wheelchair;
 b. outfitting the wheelchair with a system for receiving a control signal from the joint movement detection device and for generating an output of electro-motive force;
 wherein the method preserves a propulsive movement pattern performed by the user, and wherein the method preserves a user's ability to enact exertion of muscle-generated force for braking, propelling, and steering of the wheelchair.

* * * * *